US012599613B2

(12) United States Patent
Park et al.

(10) Patent No.: US 12,599,613 B2
(45) Date of Patent: Apr. 14, 2026

(54) COMPOSITION COMPRISING DUTASTERIDE

(71) Applicant: Chong Kun Dang Pharmaceutical Corp., Seoul (KR)

(72) Inventors: Tae Hyun Park, Gyeonggi-do (KR); Ki Seong Ko, Gyeonggi-do (KR); So Hyun Park, Gyeonggi-do (KR); Sang Myoung Noh, Gyeonggi-do (KR); Jong Lae Lim, Gyeonggi-do (KR)

(73) Assignee: Chong Kun Dang Pharmaceutical Corp. (KR)

( * ) Notice: Subject to any disclaimer, the term of this patent is extended or adjusted under 35 U.S.C. 154(b) by 1148 days.

(21) Appl. No.: 17/413,450

(22) PCT Filed: Dec. 13, 2019

(86) PCT No.: PCT/KR2019/017738
§ 371 (c)(1),
(2) Date: Jun. 11, 2021

(87) PCT Pub. No.: WO2020/122681
PCT Pub. Date: Jun. 18, 2020

(65) Prior Publication Data

US 2022/0054508 A1 Feb. 24, 2022

(30) Foreign Application Priority Data

Dec. 14, 2018 (KR) .......................... 1020180162464

(51) Int. Cl.
*A61K 31/58* (2006.01)
*A61K 47/22* (2006.01)

(52) U.S. Cl.
CPC .............. *A61K 31/58* (2013.01); *A61K 47/22* (2013.01)

(58) Field of Classification Search
CPC ...................................................... A61K 31/58
See application file for complete search history.

(56) References Cited

U.S. PATENT DOCUMENTS

| | | | |
|---|---|---|---|
| 2003/0236236 A1 | 12/2003 | Chen et al. | |
| 2006/0204588 A1 | 9/2006 | Liversidge | |
| 2010/0048598 A1 | 2/2010 | Kandavilli et al. | |
| 2018/0207146 A1* | 7/2018 | Ahn ....................... | A61K 31/58 |

FOREIGN PATENT DOCUMENTS

| | | | | |
|---|---|---|---|---|
| CN | 106659678 | | 5/2017 | |
| CN | 103169712 | | 10/2017 | |
| CN | 108430460 | | 8/2018 | |
| JP | 2017-521462 | | 8/2017 | |
| KR | 10-1055412 | B1 | 8/2011 | |
| KR | 10-1467568 | B1 | 12/2014 | |
| KR | 10-2016-0010962 | A | 1/2016 | |
| KR | 10-1679380 | | 11/2016 | |
| KR | 10-1745425 | B1 | 6/2017 | |
| WO | WO-2004105694 | A2 * | 12/2004 | ......... A61B 17/0483 |
| WO | 2006-099121 | A2 | 9/2006 | |
| WO | 2010-015556 | A1 | 2/2010 | |
| WO | WO 2016/013829 | | 1/2016 | |
| WO | 2016-104889 | A1 | 6/2016 | |
| WO | 2017-043913 | A1 | 3/2017 | |
| WO | 2017-196148 | A1 | 5/2017 | |
| WO | WO 2017116190 | | 7/2017 | |
| WO | 2019-012353 | A1 | 1/2019 | |

OTHER PUBLICATIONS

Strickley (Pharmaceutical Research, vol. 21, No. 2, Feb. 2004) (Year: 2004).*
EP Extended Search Report in European Appln. No. 19895962.9, dated Sep. 30, 2022, 10 pages.
Office Action in Brazilian Appln. No. BR112021011504-8, mailed on Oct. 16, 2023, 8 pages (with English translation).
Office Action in Chinese Appln. No. 201980082190.7, mailed on Nov. 23, 16 pages (with English translation).
Office Action in European Appln. No. 19895962.9, mailed on Nov. 3, 2023, 9 pages.
Wilkinson et al., "Lipid based intramuscular long-acting injectables: Current state of the art," European Journal of Pharmaceutical Sciences, Nov. 1, 2022, 178:106253.
International Search Report for PCT/KR2019/017738 mailed Apr. 6, 2020. 4 pages.
Office Action for KR10-2019-0166531 submitted Mar. 14, 2021 and English translation. 8 pages.
IN Office Action in Indian Appln. No. 202117026986, dated Dec. 2, 2021, 5 pages (with English Translation).
KR Notice of Allowance in Korean Appln. No. 10-2019-0166531, dated Nov. 24, 2021, 7 pages (with Machine Translation).
PCT Written Opinion in International Appln. No. PCT/KR2019/017738, dated Apr. 6, 2020, 5 pages.
JP Office Action in Japanese Appln. No. 2021-529396, dated Jun. 14, 2022, 7 pages (with English Translation).

* cited by examiner

*Primary Examiner* — John S Kenyon
*Assistant Examiner* — Rehana Ismail
(74) *Attorney, Agent, or Firm* — Fish & Richardson P.C.

(57) ABSTRACT

A composition of the present invention relates to a composition comprising dutasteride, wherein said composition may maintain a constant concentration of dutasteride in blood and continuously release a drug thereof for a long period of time while not precipitating dutasteride in a solid form when being administered into the human body, and also has an excellent safety without causing local irritations in an administration site.

12 Claims, 2 Drawing Sheets

[Fig. 1]
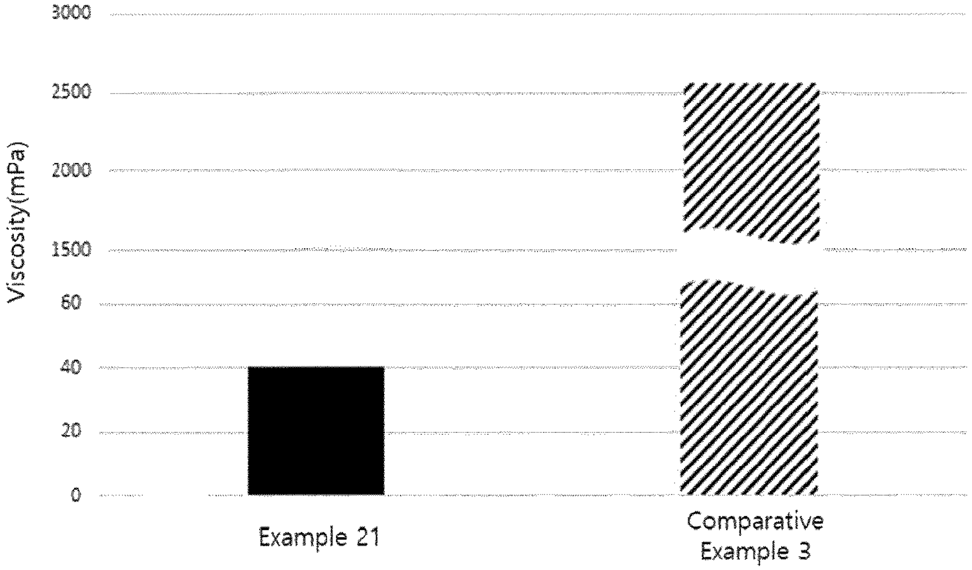
[Fig. 2]
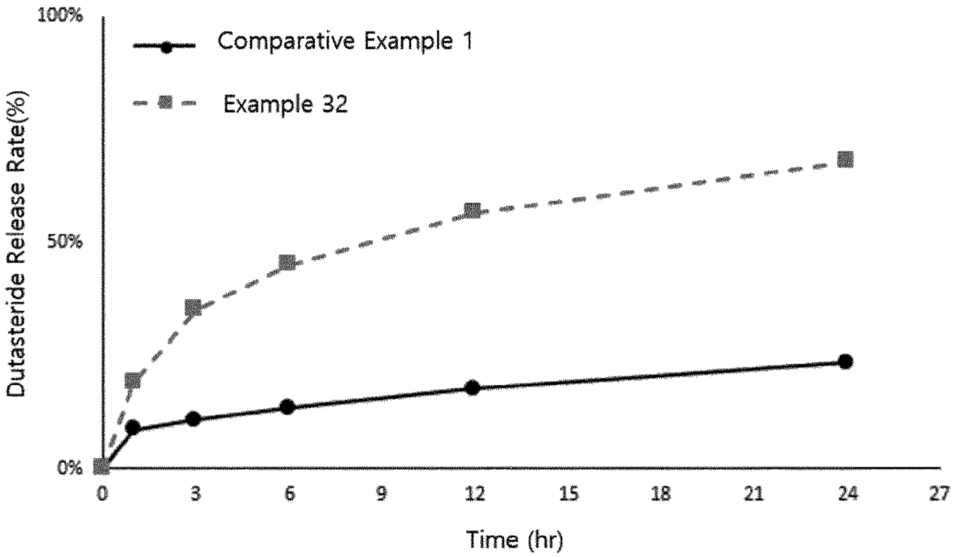
[Fig. 3]
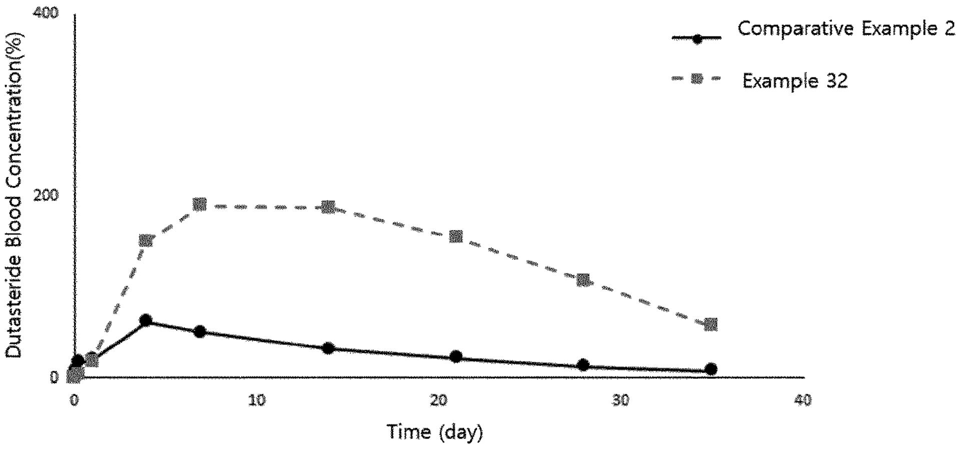

[Fig. 4]
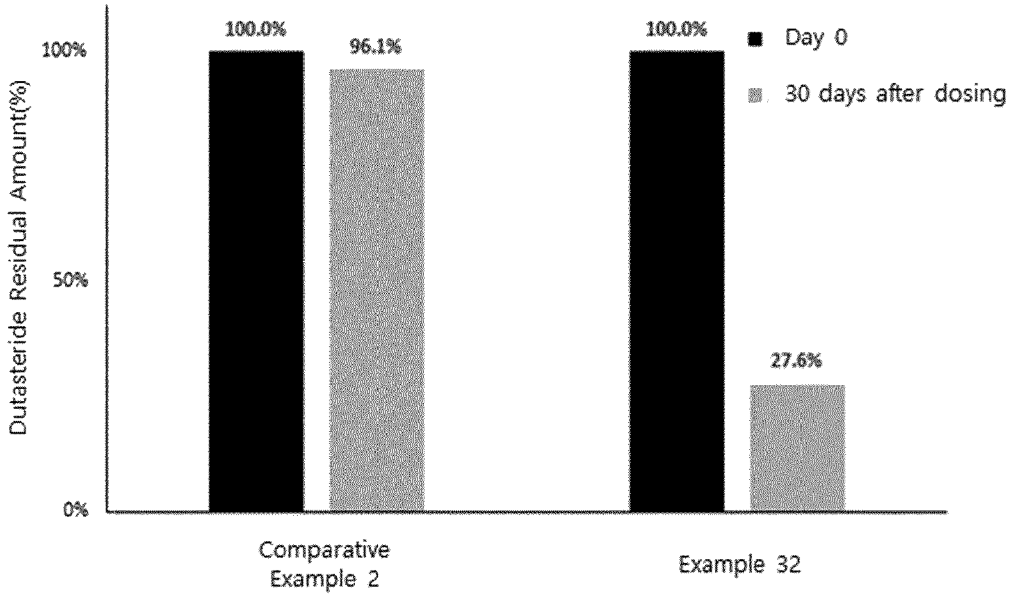
[Fig. 5]
| After Adminstration | 7 days | 14 days | 30 days | 60 days |
|---|---|---|---|---|
| **Example 21** | 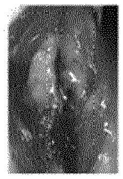 | 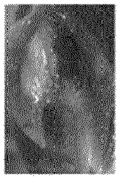 | 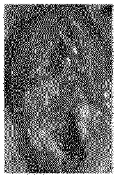 | 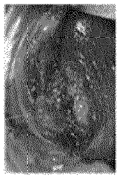 |

COMPOSITION COMPRISING DUTASTERIDE

TECHNICAL FIELD

The present invention relates to a composition containing dutasteride as a pharmacologically active substance.

BACKGROUND ART 5-alpha-reductase is a biological catalyst which reduces a male hormone, i.e., testosterone into dehydrotestosterone (DHT) in prostates, trichocysts, sebaceous glands, etc. Said dehydrotestosterone is known to be involved in hair loss, benign prostatic hyperplasia and the like. Thus, 5-alpha-reductase inhibitors for suppressing the production of dehydrotestosterone in tissues have been used as a therapeutic agent for benign prostatic hyperplasia and may be also used in preventing and treating hair loss.

Benign prostatic hyperplasia (BPH), which is one of the representative senile diseases, refers to a disease, in which an enlarged prostate presses on the urethra located at the bottom of the bladder and thus causes dysuria. The causes of benign prostatic hyperplasia are an advanced age, an effect of the male hormone and the like. Dehydrotestosterone converted from testosterone by means of 5-alpha-reductase in the prostate has an influence on the development and enlargement of the prostate and thus causes benign prostatic hyperplasia. This disease may be treated with a surgery for removing a prostate tissue, but there is a limit to eligible subjects because most of its target patients are the elderly. Thus, simple pharmacotherapy is preferred due to some problems such as post-operative side effects, recurrence and the like. As this pharmacotherapy, 5-alpha-reductase inhibitors may alleviate dysuria by selectively suppressing the production of dehydrotestosterone, expressing an effect of activating antiandrogen, and reducing an enlarged size of the prostate.

Also, hair loss refers to a state in which the number of hairs lost becomes more than an average thereof, and occurs due to various causes such as genetic factors, nutritional deficiency, stress, etc. Male pattern hair loss, which is the most common type of hair loss, is known to be caused by excessive dehydrotestosterone. Particularly, dehydrotestosterone is known to cause male pattern hair loss by causing a decline in energy production and a suppression of protein synthesis around follicles, suppressing the proliferation of follicular cells, and inducing proteins which cause hair loss. Also, a tissue in an area with hair loss is known to have a higher activity of 5-alpha-reductase than other scalp tissues. Thus, 5-alpha-reductase inhibitors may effectively prevent and treat male pattern hair loss by suppressing the production of dehydrotestosterone.

Out of the 5-alpha-reductase inhibitors, dutasteride suppresses all the types I and II 5-alpha-reductases and is used in treating benign prostatic hyperplasia, male pattern hair loss and the like through a use of an oral drug of 0.5 mg once a day. Dutasteride has no influence on testosterone which exhibits a male hormone action, but selectively suppresses only the production of dehydrotestosterone, and thus is recognized as a relatively safe therapeutic agent, but is characterized by expressing an effect, only if dutasteride is continuously taken for more than several months. Also, benign prostatic hyperplasia or male pattern hair loss requires an administration of the drug for a long period of time or for terms of life. Thus, although a commercial product requires only a single administration a day, there is still a limit in that patients show a low adherence to medication.

Accordingly, the present inventors have invented a composition containing dutasteride as a pharmacologically active substance. Said composition continues a concentration of the drug in blood for a long period of time when being administered into the human body, and thus may improve a patient's compliance with medication and consistently maintain a medicinal effect.

Hereinafter, prior art which may relate to the present invention has been examined.

International Patent Publication No. WO 2006/099121 discloses a nanoparticle composition of 2,000 nm or less. It is described that finasteride, dutasteride and tamsulosin may be used as an applicable drug, and it is also described that phospholipid and polyoxyethylene sorbitan monooleate may be used as a surface stabilizer. However, said patent is different from the present invention, i.e., a liquid composition containing lipid in that a composition of said patent is the composition on particles of 2,000 nm or less.

International Patent Publication No. WO 2004/105694 discloses a pharmaceutical composition containing an active ingredient, vitamin E and surfactant, and describes that a degree of dispersion of vitamin E may be increased 20% depending on the presence of a hydrophobic drug. However, said patent is different from the present invention in that said patent has no relation to a lipid composition for injection and also has a purpose of increasing the degree of dispersion depending on a composition when being diluted in water phase.

Korean Patent Registration No. KR 10-1745425 discloses an emulsion composition of oral complex preparation containing dutasteride and tadalafil, and describes a detailed dose of a main component, oil and surfactant contained in the composition. However, said patent is different from the present invention in that said patent has no relation to the lipid composition for injection and is also the emulsion composition of oral complex preparation.

International Patent Publication No. WO 2017/196148 discloses a composition of complex capsule preparation containing dutasteride and tadalafil and a preparation method thereof, and describes a composition containing a glycerol fatty acid ester derivative or a propylene glycol fatty acid ester derivative. However, said patent is different from the present invention in that said patent has no relation to the lipid composition for injection and is also the complex capsule preparation.

Korean Patent Registration No. KR 10-1055412 discloses a solidified preparation containing dutasteride, adsorbent and excipient, and describes the solidified preparation containing a coating solution by using a mixture of water-soluble or waterinsoluble polymers. However, said patent is different from the present invention in that said patent has no relation to the lipid composition for injection and is also the solidified preparation.

Korean Patent Registration No. KR 10-1467568 discloses a composition on a liquid preparation for external use containing minoxidil, and describes a composition containing minoxidil which has an improved dermal retention and hair growing effect. However, said patent is different from the present invention in that said patent has no relation to the lipid composition for injection and is also the composition of preparation for external use.

International Patent Publication No. WO 2010/015556 discloses a membraneforming liquid dosage form using an active ingredient selected from finasteride or Eriobotrya

*Japonica* leaf extract and said patent describes a composition of dosage form to release a drug for hair and scalp. However, said patent is different from the present invention in that said patent has no relation to the lipid composition for injection and is also the membrane-forming liquid dosage form.

PRIOR ART REFERENCES

Patent Documents (Patent Document 1) International Public Patent Notification No. WO 2006/099121
(Patent Document 2) International Public Patent Notification No. WO 2004/105694
(Patent Document 3) Korean Patent Registration Notification No. KR 10-1745425
(Patent Document 4) International Public Patent Notification No. WO 2017/196148
(Patent Document 5) Korean Patent Registration Notification No. KR 10-1055412
(Patent Document 6) Korean Patent Registration Notification No. KR 10-1467568
(Patent Document 7) International Public Patent Notification No. WO 2010/015556

DISCLOSURE OF INVENTION

Technical Problem

An objective of the present invention is to provide a composition with an improved patient's compliance with medication by sustaining a concentration of dutasteride in blood for a long period of time when being administered into the body.

Solution to Problem

This is described in detail as follows. Meanwhile, each description and embodiment disclosed in the present invention may be applied to other descriptions and embodiments thereof, respectively. In other words, all the combinations of various elements disclosed in the present invention fall within the scope of the present invention. Also, it may not be seen that the scope of the present invention is limited to the specific descriptions described below.

The present invention provides a composition containing dutasteride, lipid and an organic solvent.

Said composition according to the present invention may enhance a patient's compliance with medication and extend a duration time of medicinal effect because such composition does not cause the precipitation of dutasteride in an administration site when being administered into the human body and has an excellent sustained release capable of maintaining a constant concentration of dutasteride in blood for a long period of time. Also, said composition according to the present invention has an excellent safety which does not cause local irritation symptoms such as hardening, redness, inflammation, etc. in an administration site.

Particularly, in the present invention, said composition may be a composition containing: a) dutasteride, optical isomers thereof or pharmaceutically acceptable salts thereof; b) lipid; and c) an organic solvent.

In the present invention, dutasteride means a compound represented by the following formula 1, optical isomers thereof or pharmaceutically acceptable salts thereof:

[Formula 1]

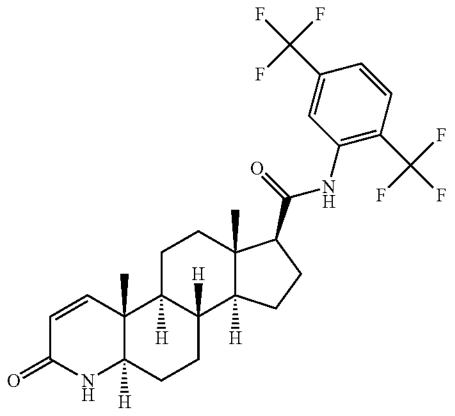

Said dutasteride, which is a drug for suppressing a male hormone, i.e., androgen, is used in treating benign prostatic hyperplasia and male pattern alopecia. Dehydrotestosterone, converted from testosterone in the prostate, is a hormone for causing benign prostatic hyperplasia and male pattern hair loss by increasing a size of the prostate and reducing follicles, and testosterone is converted into dehydrotestosterone by means of 5-alpha-reductase. Dutasteride suppresses 5-alpha-reductase and thus decreases the production of dehydrotestosterone. Through an effect of blocking the hormone, i.e., dehydrotestosterone, dutasteride is also used in treating benign prostatic hyperplasia, male pattern alopecia and hypertrichosis or used as an adjuvant for treatment after radical prostatectomy. However, this drug is characterized by expressing a medicinal effect, only when being taken for a long period of several months or more, and its products are now commercially available as an oral drug which requires a single use a day.

Dutasteride, i.e., a pharmacologically active substance of the present invention is a drug of the same classes as finasteride which is used for the same purpose as 5-alpha-reductase inhibitors. However, dutasteride blocks both type 1 and 2 5-alpha-reductases and thus may further reduce the production of dehydrotestosterone compared to finasteride which blocks the type 2 only.

A content of dutasteride contained in the composition of the present invention may be contained in an amount of about 1 to 50 wt %, particularly in an amount of about 1 to 20 wt %, more particulary in an amount of about 1 to 15 wt %, even more particulary 2 to 12 wt % with regard to the total weight of said composition.

In the present invention, lipid refers to a hydrophobic substance which may be mixed with dutasteride, as a substance which does not melt in water but melts in a non-polar solvent. Said lipid stays in an administration site along with dutasteride when being administered into the human body and then plays a role to prevent dutasteride from being precipitated into a solid in the administration site. Also, said lipid is slowly absorbed in vivo with an elapse of time and then has an influence on the release and absorption of dutasteride. This dutasteride administered into the human body along with the lipid homogencously stays in the administration site and is prevented from being precipitated there and thus may be constantly released into blood. In the present invention, lipid may be selected from the group consisting of tocopherol, tocopherol acetate, castor oil, safflower oil, sesame oil, olive oil, almond oil, *camellia* oil, corn oil, cottonseed oil, soybean oil, medium chain triglyceride (MCT), pharmaceutically acceptable salts thereof and mixtures thereof, and particularly may be selected from the group consisting of tocopherol, tocopherol acetate, pharmaceutically acceptable salts thereof and mixtures thereof, but is not limited thereto.

A content of said lipid may be adjusted within the range which may prevent dutasteride from being precipitated and exhibit a sustained release, and particularly may be contained in an amount of about 8 to 90 wt %, more particularly about 8 to 70 wt %, even more particularly 13 to 70 wt % with regard to the total weight of the composition.

According to a specific experimental example of the present invention, it was identified that the inventive composition containing lipid does not precipitate dutasteride in a form of solid powder and a dissolution rate thereof is slowly increased with an elapse of time to maintain a constant concentration of dutasteride in blood for a long period of time (FIGS. 2 to 4).

In the present invention, an organic solvent serves as a co-solvent added for solubilization of dutasteride, makes it easy to prepare a composition containing dutasteride, and provides convenience for administration by reducing a viscosity of the composition. In the present invention, the organic solvent may be selected from the group consisting of N-methyl-2-pyrrolidone, dimethyl sulfoxide, benzyl benzoate, benzyl alcohol, dimethylacetamide, ethanol, pharmaceutically acceptable salts thereof and mixtures thereof, and particularly may be N-methyl-2-pyrrolidone, dimethyl sulfoxide or benzyl benzoate, but is not limited thereto.

A content of said organic solvent may be adjusted within the range which may exhibit such a viscosity of the composition that is easily administered into the human body, and particularly may be contained in an amount of about 10 to 85 wt %, and more particularly about 10 to 82 wt %, even more particularly about 23 to 82 wt % with regard to the total weight of the composition.

In the present invention, a content of each ingredient in the above composition may be adjusted within the range which may prevent dutasteride from being precipitated, exhibit a sustained release and exhibit such a viscosity of the composition that is easily administered into the human body, and particularly said composition may contain dutasteride in an amount of about 1 to 20 wt %, optical isomers thereof or pharmaceutically acceptable salts thereof, lipid in an amount of 13 to 70 wt % and organic solvent in an amount of 10 to 82 wt %, more particularly said composition may contain dutasteride in an amount of 1 to 15 wt %, optical isomers thereof or pharmaceutically acceptable salts thereof, lipid in an amount of 13 to 70 wt % and organic solvent in an amount of 23 to 82 wt %, and even more particularly said composition may contain dutasteride in an amount of 2 to 12 wt %, lipid in an amount of 13 to 70 wt % and organic solvent in an amount of 23 to 82 wt % with regard to the total weight of the composition.

According to a specific experimental example of the present invention, it was identified that the composition of the present invention contains the organic solvent and thus the viscosity thereof is decreased to facilitate its administration into the human body (FIG. 1).

The composition of the present invention may be prepared simply by dissolving dutasteride in lipid and the organic solvent, may be easily administered into the human body through injection, and may maintain a concentration of dutasteride in blood for more than one week, particularly for more than one month while not causing a precipitation phenomenon of dutasteride, and thus the inventive composition shows an excellent sustained release.

The composition of the present invention does not contain sorbitan unsaturated fatty acid ester but is capable of showing an excellent sustained release without sorbitan unsaturated fatty acid ester.

Also, dutasteride, i.e., a pharmacologically active substance of the present invention is known as a drug which generally has good safety even when being administered into the entire body for a long period of time. However, when being administered into a localized area, for example, through an ointment preparation or an injection, in particular through the injection, dutasteride causes irritations such as localized edema, redness, hardening, etc. to an administration site and thus its application is limited. Accordingly, the present invention provides a composition with an excellent safety, which continuously releases an active substance, i.e., dutasteride for a long period of time and also does not cause irritation symptoms to the localized area such as hardening, redness, inflammation, etc., which may occur when being administered into the localized area.

The composition of the present invention may be a composition for treating one disease selected from the group consisting of benign prostatic hyperplasia, androgenetic alopecia and hypertrichosis. Also, the composition of the present invention may be used as an adjuvant for treatment after radical prostatectomy.

The composition of the present invention may be parenterally administered, for example locally administered, and particularly administered through an injection. A route of said injection administration is available in any form of administration among subcutaneous injection, intradermal injection and intramuscular injection, and the administration form may be appropriately selected according to a purpose of administering the composition. For example, if the composition of the present invention is used in treating benign prostatic hyperplasia, this composition may be administered into around the prostate through an injection. In this case, said composition may slowly release an active ingredient, i.e., dutasteride under the skin. Also, if the composition of the present invention is used in treating alopecia, this composition may be administered through an injection into a certain area of the head which requires hair growth. In this case, said composition may slowly release the active ingredient, i.e., dutasteride under the scalp skin.

A dosage of the composition of the present invention is the same as the known dosage of the pharmacologically active substance used herein, but may vary depending on a patient's disease type, degree of symptom, age, gender, etc.

Also, the present invention further provides methods and uses for sustaining the pharmacological effect by sustaining release of the pharmacologically active substance by administering said composition into mammals inculding humans.

A detailed content of said composition is the same as described as above.

Advantageous Effects of Invention

According to the present invention, a composition containing dutasteride, lipid and an organic solvent is a pharmaceutical composition which may constantly maintain a blood level of the drug substance when being administered into the human body, and which does not precipitate a pharmacologically active substance in a solid form in an administration site, thus showing an excellent safety.

BRIEF DESCRIPTION OF DRAWINGS

FIG. 1 is a graph of showing a viscosity of Comparative Example 3 and Example 21.

FIG. 2 is a graph of showing an in vitro drug release behavior of Comparative Example 1 and Example 32.

FIG. 3 is a graph of showing an in vivo drug release behavior of Comparative Example 2 and Example 32.

FIG. 4 is a graph of showing an in vivo drug residual amount in an administration site of Comparative Example 2 and Example 32.

FIG. 5 is an image of identifying an in vivo safety of a composition of Example 21.

MODE FOR THE INVENTION

Hereinafter, the present invention will be described in more detail through the following examples and experimental examples. However, the following examples and experimental examples are provided only for the purpose of illustrating the present invention, and thus the scope of the present invention is not limited thereto.

The additives used in the present invention were the excipients according to the standards of the pharmacopoeia and a reagent purchased from Aldrich, Croda.

[Examples 1 to 38] Preparation of the Inventive Pharmaceutical Composition

Examples 1 to 38

A preparation of the present invention was produced by using the ingredients and contents as shown in the following tables 1 to 3.

Particularly, an active ingredient, i.e, dutasteride was mixed with an organic solvent, and then dissolved at room temperature (25° C.) with a stirrer under the condition of 1,000-3,000 rpm for 0.5-1 hour, after which the presented lipid was added into the resulting solution. After that, the resulting mixture was dissolved in the stirrer under the condition of about 1,000-3,000 rpm for about 5-30 minutes to prepare a pharmaceutical composition in a liquid phase.

TABLE 1

| | Examples | | | | | | | | | | |
|---|---|---|---|---|---|---|---|---|---|---|---|
| (Unit: ms) | 1 | 2 | 3 | 4 | 5 | 6 | 7 | 8 | 9 | 10 | 11 |
| Dutasterid | 9 | 9 | 9 | 9 | 9 | 9 | 9 | 9 | 27 | 27 | 27 |
| Tocopherol | | | | | | | | | 150 | 300 | 150 |
| Tocopherol acetate | 15 | | | | | | | | | | |
| Castor oil | | | | | | | | | | | |
| Safflower oil | | 136 | | | | | | | | | |
| Sesame oil | | | 136 | | | | | | | | |
| Olive oil | | | | 136 | | | | | | | |
| Almond oil | | | | | 136 | | | | | | |
| Camellia oil | | | | | | | | | | | |
| Corn oil | | | | | | 136 | | | | | |
| Cottonseed oil | | | | | | | 136 | | | | |
| Soybean oil | | | | | | | | 136 | | | |
| Medium-chain triglyceride(MCT) | | | | | | | | | | | |
| N-methylpyrrolidone | 45 | 45 | 45 | 45 | 45 | 45 | 45 | 45 | 101 | 101 | 101 |
| Dimethylsulfoxide | 29 | 29 | 29 | 29 | 29 | 29 | 29 | 29 | | | |
| Benzyl benzoate | | | | | | | | | | | |
| Benzyl alcohol | | | | | | | | | | | 101 |
| Dimethyl acetamide | | | | | | | | | | | |
| Ethanol | | | | | | | | | | | |

TABLE 2

| | Examples | | | | | | | | | | | | |
|---|---|---|---|---|---|---|---|---|---|---|---|---|---|
| (Unit: ms) | 12 | 13 | 14 | 15 | 16 | 17 | 18 | 19 | 20 | 21 | 22 | 23 | 24 |
| Dutasterid | 27 | 27 | 27 | 27 | 27 | 27 | 27 | 27 | 27 | 56 | 27 | 27 | 27 |
| Tocopherol | 150 | 300 | 300 | 229 | 152 | 150 | 300 | 100 | 100 | 312 | | | |
| Tocopherol acetate | | | | | | | | | | | | | |
| Castor oil | | | | | | 68 | | 33 | 126 | | 128 | 133 | 78 |
| Safflower oil | | | | | | | | | | | | | |
| Sesame oil | | | | | | | | | | | | | |
| Olive oil | | | | | | | | | | | | | |
| Almond oil | | | | | | | | | | | | | |
| Camellia oil | | | | | | | | | | | | | |
| Corn oil | | | | | | | | | | | | | |
| Cottonseed oil | | | | | | | | | | | | | |
| Soybean oil | | | | | | | | | | | | | |
| Medium-chain triglyceride(MCT) | | | | | | | | | | | | | |
| N-methylpyrrolidone | | | | | | 101 | 101 | 101 | 101 | 210 | | 101 | |
| Dimethylsulfoxide | 87 | | | | | | 33 | 33 | 33 | 68 | | | |
| Benzyl benzoate | | 300 | 450 | | | | 100 | 50 | | | | 100 | |
| Benzyl alcohol | | | | 229 | 305 | | | | | | 200 | | |
| Dimethyl acetamide | | | | | | | | | | | | | 136 |
| Ethanol | | | | | | | | | | | | | |

TABLE 3

| | Examples | | | | | | | | | | | | | |
|---|---|---|---|---|---|---|---|---|---|---|---|---|---|---|
| (Unit: mg) | 25 | 26 | 27 | 28 | 29 | 30 | 31 | 32 | 33 | 34 | 35 | 36 | 37 | 38 |
| Dutasterid | 27 | 27 | 27 | 56 | 56 | 9 | 6 | 27 | 27 | 27 | 27 | 56 | 9 | 9 |
| Tocopherol | | 300 | | 312 | 312 | | | 300 | 300 | 300 | 150 | 156 | | |
| Tocopherol acetate | | | | | | 50 | 5 | | | | | | | |
| Castor oil | 275 | | 700 | | | | | | | | | | | |
| Safflower oil | | | | | 263 | | | | | | | | | |
| Sesame oil | | | | 263 | | | | | | | | | | |
| Olive oil | | | | | | | | | | | | | | |
| Almond oil | | | | | | | | | | | | | | |
| Camellia oil | | | | | | | | | | | | | 136 | |
| Corn oil | | | | | | | | | | | | | | |
| Cottonseed oil | | | | | | | | | | | | | | |
| Soybean oil | | | | | | | | | | | | | | |
| Medium-chain triglyceride(MCT) | | | | | | | | | | | | | | 50 |
| N-methylpyrrolidone | | 101 | | 210 | 210 | 33 | 30 | 101 | 120 | 120 | 101 | 210 | 45 | 34 |
| Dimethylsulfoxide | 408 | | 408 | 68 | 68 | | 20 | 33 | | | | 68 | 29 | 29 |
| Benzyl benzoate | | 100 | 100 | | | | | | 100 | 200 | | | | |
| Benzyl alcohol | | | | | | | | | | | | | | |
| Dimethyl acetamide | | | | | | | | | | | | | | |
| Ethanol | | | | | | | | | | | 3 | | | |

Comparative Examples 1 to 3

Comparative Examples 1 to 3

The active ingredient, i.e, a raw substance of dutasteride was used in Comparative Example 1.

In Comparative Examples 2 to 3 of the following table 4, the active ingredient, i.e, dutasteride was mixed with an organic solvent or lipid, and then dissolved at room temperature (25° C.) with the stirrer under the condition of 1,000-3,000 rpm for 0.5-12 hours to prepare a pharmaceutical composition in a liquid phase.

TABLE 4

| | Comparative Examples | | |
|---|---|---|---|
| (Unit: ms) | 1 | 2 | 3 |
| Dutasterid | 56 | 27 | 56 |
| Tocopherol | | | 312 |
| Tocopherol acetate | | | |
| Castor oil | | | |
| Safflower oil | | | |
| Sesame oil | | | |
| Olive oil | | | |
| Almond oil | | | |
| Camellia oil | | | |
| Corn oil | | | |
| Cottonseed oil | | | |
| Soybean oil | | | |
| Medium-chain triglyceride(MCT) | | | |
| N-methylpyrrolidone | | 101 | |
| Dimethylsulfoxide | | 33 | |
| Benzyl benzoate | | | |
| Benzyl alcohol | | | |
| Dimethyl acetamide | | | |
| Ethanol | | | |

[Experimental Example 1] Identification of Content of Pharmacological Active Ingredients in Composition To identify a content of a pharmacologically active substance in the pharmaceutical composition prepared through Examples of the present invention, the content of dutasteride, used as the pharmacologically active substance, was identified and the results thereof were shown in the following table 5. The content of dutasteride was quantified with HPLC and analysis conditions were as follows.

<HPLC Analysis Conditions for Dutasteride>

Column: 4.6 mm×250 mm, 5 μm

Column temperature: 35° C.

Detector: Ultraviolet absorption spectrophotometer (wavelength: 220 nm)

Flow rate: 1.0 mL/min.

Injection volume: 10 μl

Mobile phase: Water, acetonitrile and trifluoroacetic acid (48:52:0.025)

TABLE 5

| | Comparative Examples | | Examples | | | |
|---|---|---|---|---|---|---|
| (Unit: %) | 2 | 3 | 9 | 19 | 21 | 33 |
| Content | 103.1 | 100.7 | 102.0 | 101.9 | 100.5 | 98.5 |

As shown in the table 5, the pharmaceutical compositions of Comparative Example 2, Comparative Example 3, Example 9, Example 19, Example 21 and Example 33 showed a very ideal measured value within ±3% compared to a reference content (100%) of dutasteride.

[Experimental Example 2] Identification of Viscosity of Pharmaceutical Composition In Vitro A viscosity of the inventive compositions in vitro was identified through the following experiment. The viscosity of Example 21 containing dutasteride, lipid and an organic solvent, and the viscosity of Comparative Example 3 excluding the organic solvent were compared with each other with a viscosity measuring apparatus. Conditions for viscosity measurement are as follows.

<Conditions for Measuring Viscosity of Pharmaceutical Composition>

Viscometer: Rheometer (RHEOSENSE Inc.)

Analysis temperature: 25±0.5° C.

Viscosity was measured and analyzed with the rheometer in which a thermostat is installed, and the results thereof were shown in FIG. 1. The results of FIG. 1 show an average of viscosity values measured five times.

In case of Comparative Example 3 excluding the organic solvent from Example 21, the results of measuring the viscosity five times were 2,553, 2,565, 2,557, 2,547 and 2,543 mPa respectively, thus showing that an average viscosity is 2,553 mPa. On the other hand, in case of Example 21 containing dutasteride, lipid and the organic solvent, the results of measuring the viscosity five times were 40.5, 40.4, 40.4, 40.9 and 40.8 mPa respectively, thus showing that an average viscosity is 40.6 mPa. From the results, it was identified that the composition of the present invention contains the organic solvent to reduce the viscosity of the composition and thus may be easily administered into the human body.

[Experimental Example 3] Identification of Dissolution Rate of Pharmaceutical Composition In Vitro A dissolution rate of the inventive compositions in vitro was identified through the following experiment. Example 32 was filled into a disposable syringe in such an amount that corresponds to 56 mg of dutasteride and then injected into a dissolution medium, and Comparative Example 1 was directly put into a rotating basket in such an amount that corresponds to 56 mg of dutasteride. This experiment was performed according to the dissolution test method I in the 10th revision of the Korean Pharmacopocia and the conditions for dissolution are as follows.

<Conditions for Dissolution of Pharmaceutical Composition>

Dissolution method: Method I of the Korean Pharmacopoeia (Appratus I—Basket)

Dissolution medium: 900 mL of solution containing 1% w/v sodium dodecyl sulfate

Dissolution temperature: 37±0.5° C.

Rotation speed: 100 rpm

Test hour: 1, 3, 6, 12 and 24 hours

With regard to a concentration of dutasteride in a dissolution sample, a dissolution rate for 24 hours was analyzed with HPLC under the condition of Experimental Example 1 and the results thereof were shown in FIG. 2.

In case of directly administering Comparative Example 1 into the dissolution medium containing surfactants, a part of the drug only was dissolved into the dissolution medium and a dissolution rate was hardly increased with an elapse of time from one hour after. However, in case of administering Example 32 containing lipid, it was identified that dutasteride is not precipitated in a form of solid powder in the dissolution medium and a dissolution rate is slowly increased with an elapse of time.

[Experimental Example 4] Identification of PK of Pharmaceutical Composition In Vivo A drug release behavior of the inventive compositions in vivo was identified through the following experiment. Each of the compositions of Comparative Example 2 and Example 32 was filled into a disposable syringe, and then intramuscularly injected into the thigh of six SD rats (male) respectively, which were nine weeks old and weighed 300 g on average, in such an amount that corresponds to 27 mg of dutasteride.

The concentration of dutasteride in a plasma sample of SD rats was analyzed with regard to a PK (pharmacokinetic) profile by using the LC-MS/MS (liquid chromatography/mass spectrometer), and the results thereof were shown in FIG. 3.

In case of Example 32, i.e., a lipid composition containing dutasteride, it was identified that a constant blood concentration thereof is maintained for more than one month when being administered in vivo. On the other hand, in case of Comparative Example 2, i.e., a composition not containing lipid, the concentration of dutasteride in blood is very low compared to Example 32. It was identified through the following Experimental Example 5 that the cause is due to the precipitation of dutasteride in powder form at the administration site.

From the results, it was identified that the composition of the present invention maintains a constant blood concentration for more than one month and thus shows an excellent sustained release, while not precipitating dutasteride in a form of powder at the administration site.

[Experimental Example 5] Identification of Drug Residual Amount in Administration Site In Vivo Through the following experiment, the composition was administered in vivo to identify a residual amount of the drug in an administration site with an elapse of certain time. Each of the compositions of Comparative Example 2 and Example 32 was filled into a disposable syringe, and then intramuscularly injected into the thigh of six SD rats (male) respectively, which were nine weeks old and weighed 300 g on average, in such an amount that corresponds to 27 mg of dutasteride.

In 30 days later, the rats were subjected to autopsy to collect muscle tissues from an area into which the composition was administered. 20 mL of ethanol was added to the collected muscle tissues, and then crushed with a homogenizer for about 30 minutes. After that, the crushed tissues were centrifuged at 3,000 rpm for 20 minutes by using a centrifugal separator, after which supernatant thereof was collected therefrom and quantified under the analysis conditions for dutasteride in Experimental Example 1, and the results thereof were shown in FIG. 4.

It was identified for Example 32 that a residual amount of dutasteride is about 28% in an administration site in one month after administration and thus 72% of the drug administered is absorbed in vivo. On the other hand, it was identified for Comparative Example 2 that about 96% of dutasteride remains in the administration site even with an elapse of one month after administration.

From the results, it was identified that the inventive composition containing lipid is continuously absorbed in the administration site when being administered in vivo and thus may maintain a constant concentration of the drug in blood for a long period of time, but it was also identified for Comparative Example 2, i.e., the composition not containing lipid that most of the drug is not absorbed at all while staying in the administration site when being administered in vivo. This may be explained as a cause of the in vivo PK test results in Experimental Example 3.

[Experimental Example 6] Identification of Local Tolerance of Pharmaceutical Composition In Vivo The safety of the inventive composition in vivo was identified through the following experiment. The composition of Example 21 was filled into a disposable syringe, and then intramuscularly injected into the thigh of six SD rats (male), which were nine weeks old and weighed 300 g on average, in such an amount that corresponds to 27 mg of dutasteride. After administration into the SD rats, the presence of edema, redness, hardening, necrosis and exudate was identified with the naked eye from the administration site through autopsy in 7, 14, 30 and 60 days later, and the results thereof were shown in FIG. 5.

As shown in FIG. 5, it was identified that the composition of the present invention is a safe composition without irritations such as edema, redness, hardening, etc. observed from the administration site in all points of autopsy time.

The invention claimed is:

1. A parenteral composition comprising dutasteride, optical isomers thereof or pharmaceutically acceptable salts thereof, lipid and an organic solvent, wherein:

the lipid is selected from the group consisting of tocopherol, tocopherol acetate, pharmaceutically acceptable salts thereof and mixtures thereof and the lipid is present in an amount of 13 to 70 wt % with regard to the total weight of the composition.

2. The parenteral composition according to claim 1, wherein the parenteral composition does not comprise sorbitan unsaturated fatty acid ester.

3. The parenteral composition according to claim 1, wherein the organic solvent is selected from the group consisting of N-methyl-2-pyrrolidone, dimethyl sulfoxide, benzyl benzoate, benzyl alcohol, dimethylacetamide, ethanol and mixtures thereof.

4. The parenteral composition according to claim 1, wherein the organic solvent is selected from the group consisting of N-methyl-2-pyrrolidone, dimethyl sulfoxide, benzyl benzoate and mixtures thereof.

5. A method for preventing or treating benign prostatic hyperplasia or androgenetic alopecia by administering a therapeutically effective dose of a composition comprising dutasteride, optical isomers thereof or pharmaceutically acceptable salts thereof, lipid and an organic solvent to a subject in need of treatment, wherein:

the lipid is selected from the group consisting of tocopherol, tocopherol acetate, pharmaceutically acceptable salts thereof and mixtures thereof and the lipid is present in an amount of 13 to 70 wt % with regard to the total weight of the composition; and the composition is administered through an injection.

6. The method according to claim 5, wherein the composition does not comprise sorbitan unsaturated fatty acid ester.

7. The method according to claim 5, wherein a route of administration of the composition is a subcutaneous injection, an intradermal injection or an intramuscular injection.

8. A parenteral composition comprising dutasteride, optical isomers thereof or pharmaceutically acceptable salts thereof; tocopherol; N-methyl-2-pyrrolidone and dimethyl sulfoxide, wherein tocopherol is present in an amount of 13 to 70 wt % with regard to the total weight of the composition.

9. A method for preventing or treating benign prostatic hyperplasia or androgenetic alopecia by administering a therapeutically effective dose of a composition comprising dutasteride, optical isomers thereof or pharmaceutically acceptable salts thereof; tocopherol; N-methyl-2-pyrrolidone and dimethyl sulfoxide, wherein tocopherol is present in an amount of 13 to 70 wt % with regard to the total weight of the composition, and wherein the composition is administered through an injection.

10. The method according to claim 9, wherein a route of administration of the composition is a subcutaneous injection, an intradermal injection or an intramuscular injection.

11. The parenteral composition according to claim 8, wherein the parenteral composition does not comprise sorbitan unsaturated fatty acid ester.

12. The method according to claim 9, wherein the composition does not comprise sorbitan unsaturated fatty acid ester.

* * * * *